(12) United States Patent
Lee

(10) Patent No.: US 12,251,296 B2
(45) Date of Patent: Mar. 18, 2025

(54) BAND FOR PREVENTING CONTACT OF INJURY

(71) Applicant: Andrew Lee, Portland, OR (US)

(72) Inventor: Andrew Lee, Portland, OR (US)

(*) Notice: Subject to any disclaimer, the term of this patent is extended or adjusted under 35 U.S.C. 154(b) by 0 days.

(21) Appl. No.: 18/898,474

(22) Filed: Sep. 26, 2024

(65) Prior Publication Data

US 2025/0017789 A1 Jan. 16, 2025

Related U.S. Application Data

(63) Continuation of application No. 18/796,178, filed on Aug. 6, 2024.

(51) Int. Cl.
*A61F 13/00* (2024.01)
*A61F 13/62* (2006.01)
*A61F 13/56* (2006.01)

(52) U.S. Cl.
CPC ...... *A61F 13/62* (2013.01); *A61F 2013/5677* (2013.01)

(58) Field of Classification Search
CPC .......... A61F 2/82; A61F 2/34; A61F 2/30756; A61F 2/3603; A61F 2/32; A61F 2/3601; A61F 2/3609; A61F 2/4607; A61F 2/4609; A61F 2/28; A61F 5/0036; A61F 5/0069; A61F 5/0089
USPC ......................................................... 602/41
See application file for complete search history.

(56) References Cited

U.S. PATENT DOCUMENTS

| | | | | | |
|---|---|---|---|---|---|
| 5,264,218 | A | * | 11/1993 | Rogozinski | A61L 15/42 424/443 |
| 6,107,536 | A | * | 8/2000 | Dadinis | A61F 15/008 602/44 |
| 8,237,008 | B1 | * | 8/2012 | Alessandrini | A61F 13/622 602/61 |
| 8,591,447 | B2 | * | 11/2013 | DiGrazia | A61F 15/004 602/41 |

FOREIGN PATENT DOCUMENTS

| | | | | |
|---|---|---|---|---|
| DE | 4218776 A1 | * | 12/1993 | ........... A61F 13/061 |
| WO | WO-9210983 A1 | * | 7/1992 | ....... A61F 13/00038 |

OTHER PUBLICATIONS

Tanslation of DE4218776 (Year: 1993).*

* cited by examiner

*Primary Examiner* — Kim M Lewis
(74) *Attorney, Agent, or Firm* — Renaissance IP Law Group LLP

(57) ABSTRACT

An injury contact prevention band includes an injury cover portion and a fastening portion. The injury cover portion covers a part of a body including an injury. The fastening portion fastens the injury cover portion to the body. A plurality of injury opening holes cutting through a thickness of the injury cover portion to expose the injury. The fastening portion includes a first fastening member, a second fastening member, and a connecting member. The first fastening member extends from an end of the injury cover portion and has flexibility. The second fastening member extends from an other end of the injury cover portion and has flexibility. The connecting member detachably connects an end of the first fastening member and an end of the second fastening member to each other. The plurality of injury opening holes is arranged along at least one direction.

2 Claims, 8 Drawing Sheets

BAND FOR PREVENTING CONTACT OF INJURY

CROSS-REFERENCE TO RELATED APPLICATION

This application is a continuation of U.S. patent application Ser. No. 18/796,178, filed Aug. 6, 2024, the disclosure of which is incorporated herein by reference in its entirety.

The present disclosure relates to a band, and more particularly to a band that prevents contact of a patient's injury.

In general, in the case of patients who lie in bed for a long period of time due to difficulty in movement, or paralyzed patients such as paralysis of the lower body or the entire body, bedsores easily form in areas that are under pressure because of poor blood circulation and metabolism due to remaining in the same posture for a long period of time.

In order to prevent these bedsores, the patient's lying position is often changed at regular intervals to relieve the burden on the pressured area. For this purpose, it is effective for the patient to lie down on his or her side facing the left or right at regular intervals to relieve the pressure on the back and buttocks, where bedsores usually occur, while the patient is lying down.

Additionally, if an injury such as a bedsore has already occurred, if the injury comes into contact with a bed mattress or blanket, pain may be caused and injury recovery may be delayed. Even if the bedsore area comes into contact with a flexible and soft object, such as a bandage used for general injuries, it may cause pain.

To prevent such contact, bedding that supports a lying patient, such as the mat of Korean Publication No. 10-2010-0079743, has been developed. However, such bedding generally has a large volume, so it is difficult to use in small houses and is difficult or bulky to carry. In addition, although it is possible to prevent contact with the back area, contacts with other areas may not be prevented.

SUMMARY

An injury contact prevention band includes an injury cover portion and a fastening portion. The injury cover portion covers a part of a body including an injury. The fastening portion fastens the injury cover portion to the body. A plurality of injury opening holes cutting through a thickness of the injury cover portion to expose the injury. The fastening portion includes a first fastening member, a second fastening member, and a connecting member. The first fastening member extends from an end of the injury cover portion and has flexibility. The second fastening member extends from an other end of the injury cover portion and has flexibility. The connecting member detachably connects an end of the first fastening member and an end of the second fastening member to each other. The plurality of injury opening holes are arranged along at least one direction.

BRIEF DESCRIPTION OF DRAWINGS

The above and other aspects, features, and advantages of the present disclosure will be more clearly understood from the following detailed description, taken in conjunction with the accompanying drawings.

DETAILED DESCRIPTION

Hereinafter, embodiments of the present disclosure will be described in detail and clearly to such an extent that an ordinary one in the art easily implements the inventive concept.

In this specification, the inside refers to the surface or area facing the body part on which the band may be worn on the body, and the outside refers to the surface or area facing away from the body.

Figure 1:
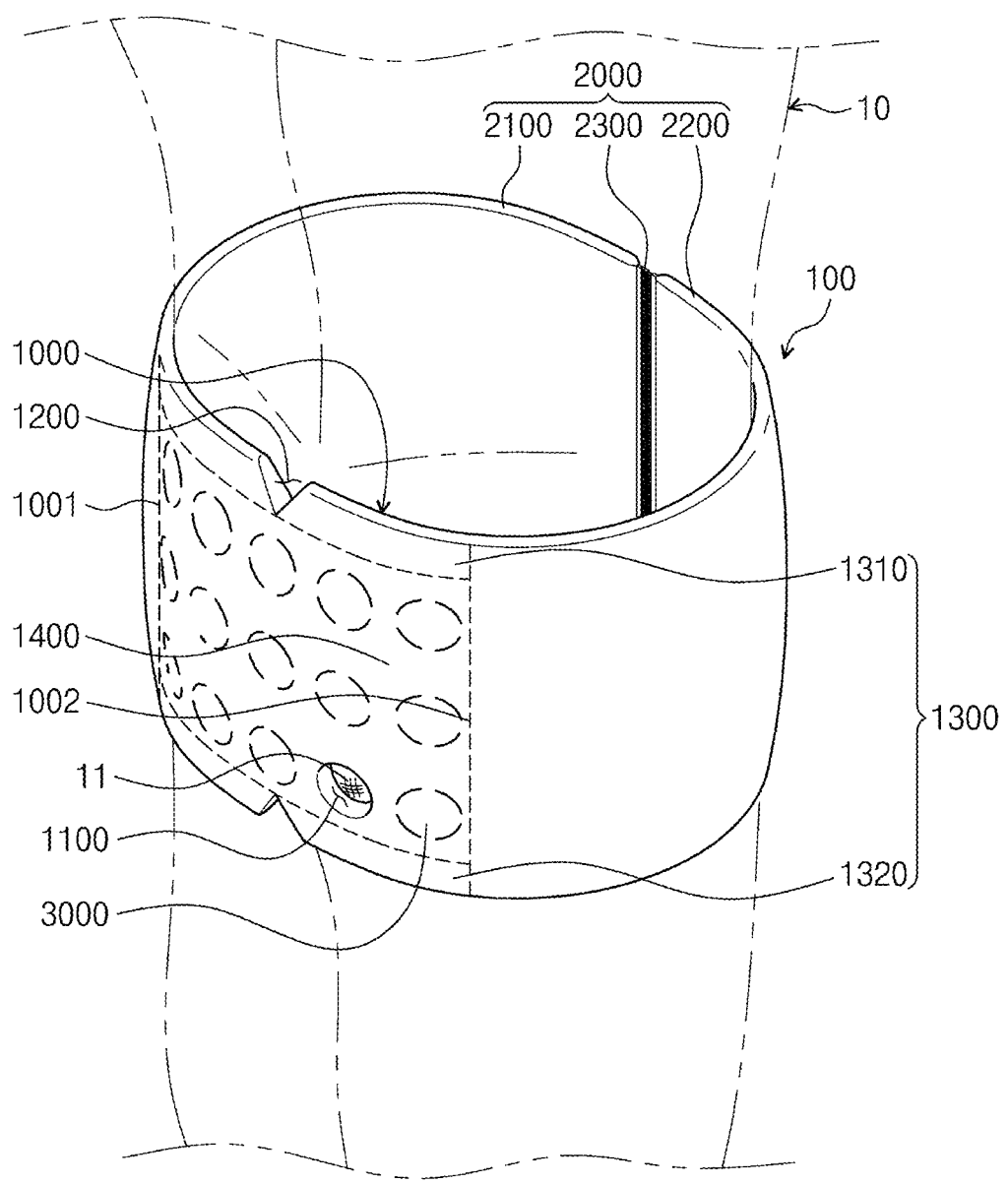
FIG. 1 is a perspective view illustrating an injury contact prevention band according to an example embodiment of the present disclosure.

FIG. 1 is a perspective view illustrating an injury contact prevention band 100 according to an embodiment. The injury contact prevention band 100 may prevent an injury or wound 11 from contacting an external object while fastened to a patient's body 10. For example, external objects may include bedding such as blankets or bed mattresses. In FIG. 1, the injury contact prevention band 100 is illustrated fastened to the pelvis portion so that the injury cover portion 1000 is positioned in a position covering the buttocks. However, unlike this, the injury contact prevention band 100 may be fastened to various parts of the body 10 such as the arm or thigh so that an injury cover portion 1000 may cover the area where the injury 11 occurs. For example, an injury or a wound may be a variety of injuries that may be painful or infected upon contact, such as bedsores, surgical sites, or skin problems. The injury contact prevention band 100 may include an injury cover portion 1000, a fastening portion 2000, and a hole cover portion 3000.

The injury cover portion 1000 is configured or designed to cover a part of the body 10 including the injury 11. In one embodiment, the injury cover portion 1000 may be flexible and/or elastic. For example, the injury cover portion 1000 may be made of a natural or synthetic material having flexibility and/or elasticity, such as leather, rubber, polyurethane, or acrylic resin. In another embodiment, the injury cover portion 1000 may have a structure in which components of different materials are combined. For example, the injury cover portion 1000 may be provided in a structure in which fabrics of different materials overlap each other to form a plurality of layers.

In one embodiment, the injury cover portion 1000 has an injury opening hole 1100 and a cut portion 1200.

The injury opening hole 1100 cuts through the entire thickness of injury cover portion 1000, or penetrates between an inner surface and an outer surface of the injury cover portion 1000 to expose, reveal, show, or display the injury 11 of the fastened body 10 to the outside. In one embodiment, a plurality of injury opening holes 1100 may be arranged along at least one direction. For example, a plurality of injury opening holes 1100 may be arranged in a grid structure. In another embodiment, the injury opening holes 1100 may be provided in various numbers and arranged in any patterns or along various directions. The injury opening hole 1100 may have a circular, square, rectangular, triangular, oval, elliptical, or any suitable shape.

Figure 2:
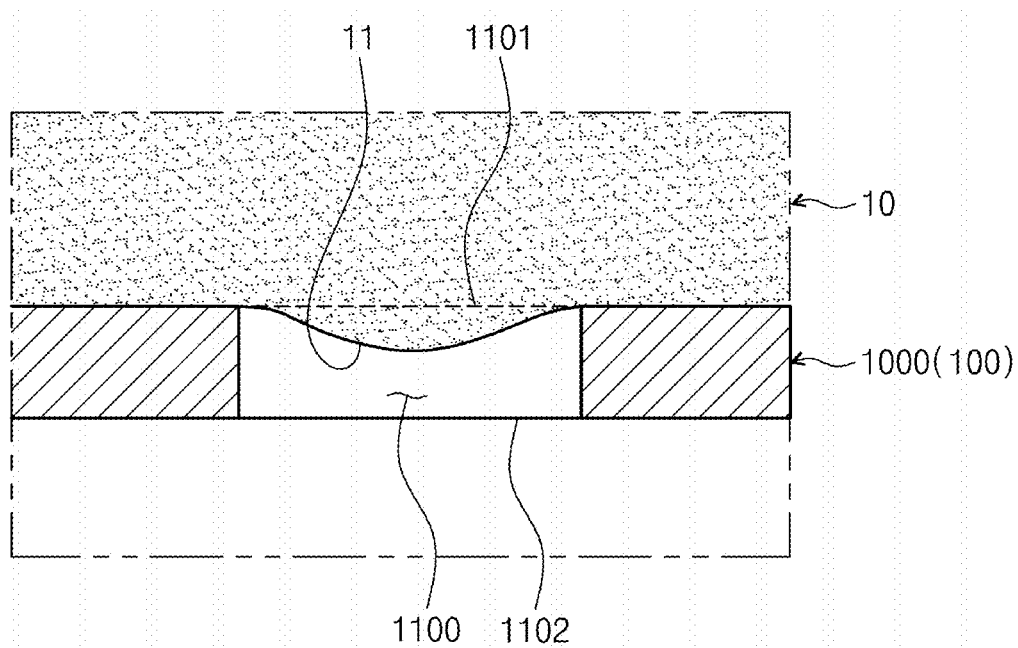
FIG. 2 is a side cross-sectional view of the area where the injury opening hole of the injury cover portion illustrated in FIG. 1 is formed, cut from the inner side to the outer side.

FIG. 2 is a side cross-sectional view of the area where the injury opening hole 1100 of the injury cover portion 1000 illustrated in FIG. 1 is positioned, cut from the inner side to the outer side. Referring to FIGS. 1 and 2, the injury contact prevention band 100 may be fastened to the body 10 so that the open injury opening hole 1100 is positioned facing the injury 11 site. The injury cover portion 1000 may be provided with a thickness greater than the protrusion height of the injury 11 depending on the protrusion height of the injury 11 from the surrounding skin. The thickness of the injury cover portion 1000 may be provided by considering the degree to which the injury cover portion 1000 is compressed by the weight of the patient wearing it. However, the thicker the injury cover portion 1000, the greater the burden on the patient, such as making it difficult to move the worn part when worn, so the thickness of the injury cover portion 1000 relative to the protrusion height of the injury may be determined by test wearing or by other experiments or simulations, by considering the above-mentioned conditions. Therefore, the injury that opens through the injury opening hole 1100 is prevented from being contacted by the injury cover portion 1000, and prevented from contact with external objects by being surrounded by the injury opening hole 1100.

Figure 3:
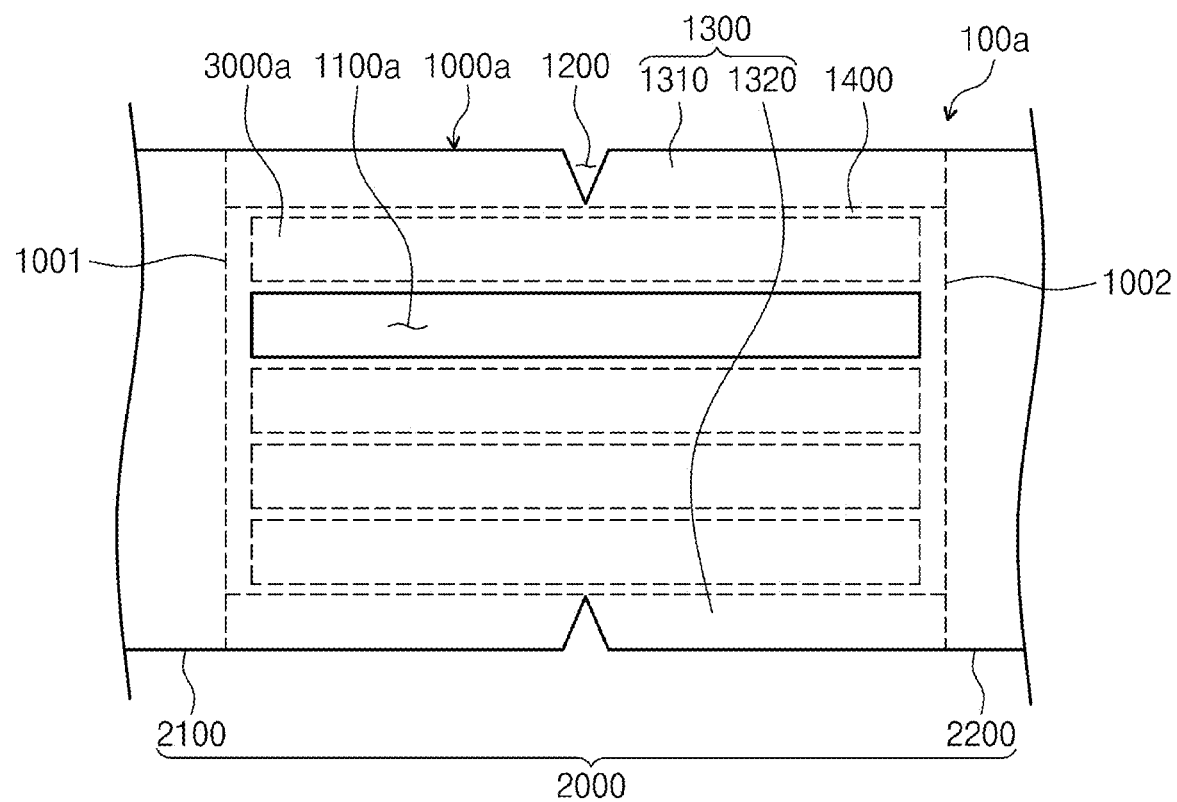
FIGS. 3 and 4 are partial front views illustrating injury contact prevention bands according to an example embodiment.
Figure 4:
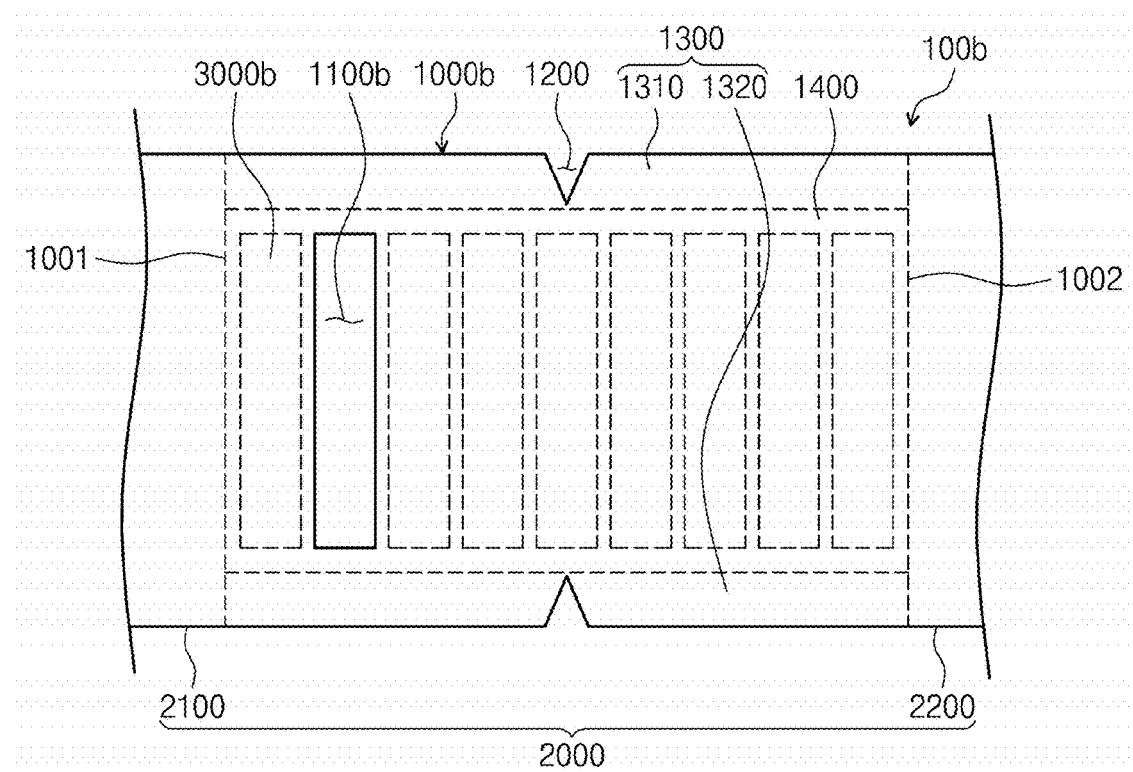

FIGS. 3 and 4 are partial front views illustrating injury contact prevention bands 100*a* and 100*b* according to an example embodiment. The injury opening holes 1100*a* and 1100*b* may have various shapes such as square or oval. For example, the injury opening holes 1100*a* and 1100*b* may be provided in a slit shape having an elongated shape in one direction. In this way, the injury opening holes 1100*a* and 1100*b* are provided in various shapes, so that the user may selectively use the injury contact prevention band 100 having the injury opening holes 1100, 1100*a* and 1100*b* suitable for the shape and size of the injury. An injury cover portion 1000*a*, having a function similar to the function of the injury cover portion 1000 of FIG. 1, is shown in FIG. 3 and an injury cover portion 1000*b* is shown in FIG. 4. Further, a hole cover portion 3000*b* having a function similar to that of the hole cover portion 3000 of FIG. 1 is shown in FIG. 4.

In the drawings of the present specification, it is illustrated that injury opening holes 1100, 1100*a* and 1100*b* of the same shape are formed in one injury contact prevention band 100. However, one injury contact prevention band 100 may have injury opening holes 1100, 1100*a* and 1100*b* of different shapes.

Referring again to FIG. 1, the cut portion 1200 may be located in the end area 1300 of the injury cover portion 1000.

The end area 1300 may be located between an end and another end of an edge area of the injury cover portion 1000. In one embodiment, the end area 1300 may include a first edge area 1310 and a second edge area 1320.

The first edge area 1310 is one of the areas between the end 1001 and the other end 1002 of the edge area of the injury cover portion 1000. The second edge area 1320 is another one of the areas between the end 1001 and the other end 1002 of the edge area of the injury cover portion 1000.

In one embodiment, the cut portion 1200 may be located in the middle between the end 1001 and the other end 1002 of the injury cover portion 1000 in each of the first edge area 1310 and the second edge area 1320. The cut portion 1200 is formed by cutting into a recessed shape from the outer perimeter the injury cover portion 1000 toward the central area 1400. The cut portion 1200 may have a wedge shape that becomes wider as it moves away from the central area 1400.

As described above, the cut portion 1200 may be formed or position in the end area 1300, so that when the injury contact prevention band 100 is fastened to the body 10, each part cut by the cut portion 1200 in the end area may move more freely and flexibly inward and outward according to the curve of the body 10, thereby the lifting part from the skin caused by mutual interference may be reduced. The farther the part of the injury cover portion 1000 is from the central area 1400, the more movement may occur relative to the skin when the body 10 moves, and the part that is lifted from the skin has more movement compared to the part that is not lifted. The part that is lifted from the skin causes more movement than the part that is not lifted, which may cause pain and injury due to chafing of the skin. Therefore, as described above, the cut portion 1200 may reduce the lifted area and prevent skin chafing due to such lifting.

The fastening portion 2000 fastens the injury cover portion 1000 to the body 10. In one embodiment, the fastening portion 2000 includes a first fastening member 2100, a second fastening member 2200, and a connecting member 2300.

The first fastening member 2100 extends from the end 1001 of the injury cover portion 1000. The first fastening member 2100 may be flexible and/or elastic.

The second fastening member 2200 extends from the other end 1002 of the injury cover portion 1000. The second fastening member 2200 may be flexible and/or elastic.

For example, the first fastening member 2100 and the second fastening member 2200 may be made of natural or synthetic materials having flexibility and/or elasticity, such as leather, rubber, polyurethane, or acrylic resin. In another embodiment, the first fastening member 2100 and the second fastening member 2200 may have a structure in which different materials are combined. For example, the first fastening member 2100 and the second fastening member 2200 may be provided in a structure in which fabrics made of different materials overlap each other to form a plurality of layers. In one embodiment, the injury cover portion 1000, the first fastening member 2100, and the second fastening member 2200 may be provided as an integrated body having the same material and structure.

The connecting member 2300 detachably connects the end of the first fastening member 2100 and the end of the second fastening member 2200 to each other. In one embodiment, the connecting member 2300 may be provided in a zipper manner. Alternatively, the connecting member 2300 may be provided in various types of fastening structures that allow the end of the first fastening member 2100 and the end of the second fastening member 2200 to be attachable to each other and detachable from each other. For example, the connecting member 2300 may be provided in various structures, such as a Velcro® or button fastening structure.

Figure 5:
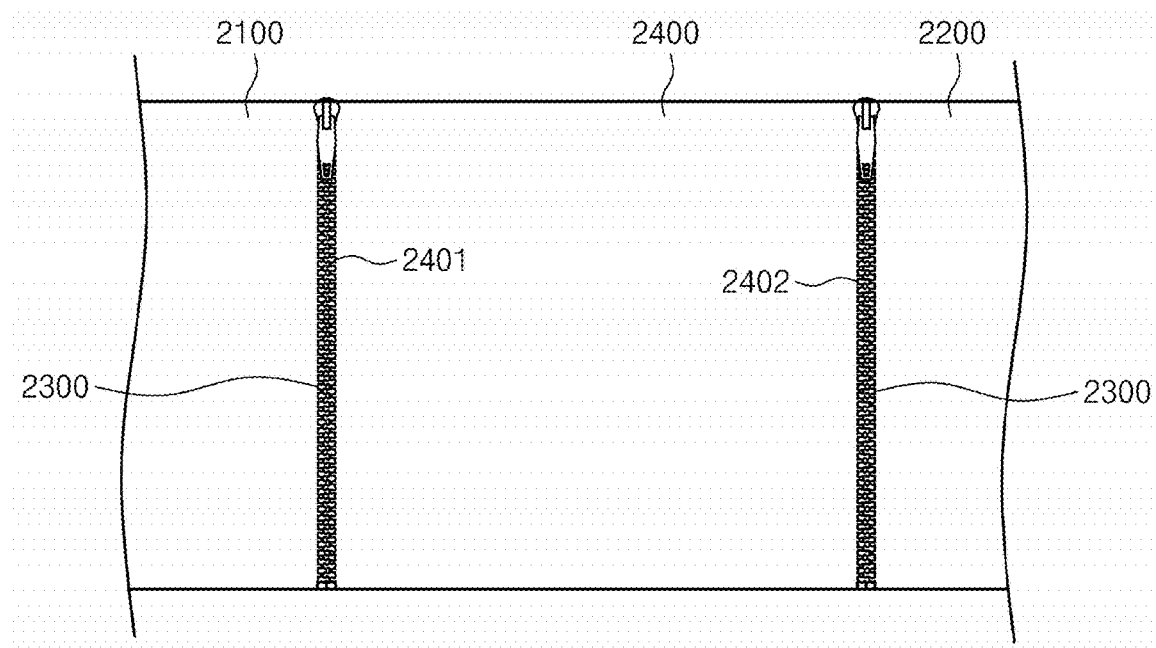
FIG. 5 is a front view illustrating an example of a fastening portion to which an extension member is connected.

FIG. 5 is a front view illustrating an example of a fastening portion to which an extension member is connected. Referring to FIG. 5, the fastening portion 2000 may further include an extension member 2400. The extension member 2400 extends the length of the fastening portion 2000. In one embodiment, the end 2401 of the extension member 2400 is provided to be detachable from the end of the first fastening member 2100. And the other end 2402 of the extension member 2400 is provided to be detachable from the end of the second fastening member 2200. A fastening configuration detachable from the configuration of the connecting member 2300 that is provided at the end of the first fastening member 2100 may be provided at the end 2401 of the extension member 2400. A fastening configuration detachable from the configuration of the connecting member 2300 that is provided at the end of the second fastening member 2200 may be provided at the other end 2402 of the extension member 2400. For example, when the connecting member 2300 is provided as a zipper structure, A configuration of a zipper detachable from the zipper configuration of the connecting member 2300 that is provided at the end of the first fastening member 2100 may be provided at the end 2401 of the extension member 2400. Another configuration of the zipper detachable from the zipper configuration of the connecting member 2300 that is provided at the end of the second fastening member 2200 may be provided at the other end 2402 of the extension member 2400. Alternatively, the connecting member 2300 and the extension member 2400 may be fastened to each other using a Velcro® or button structure. The extension member 2400 allows the length of the injury contact prevention band 100 to be adjusted according to the circumference of the body part.

Figure 6:
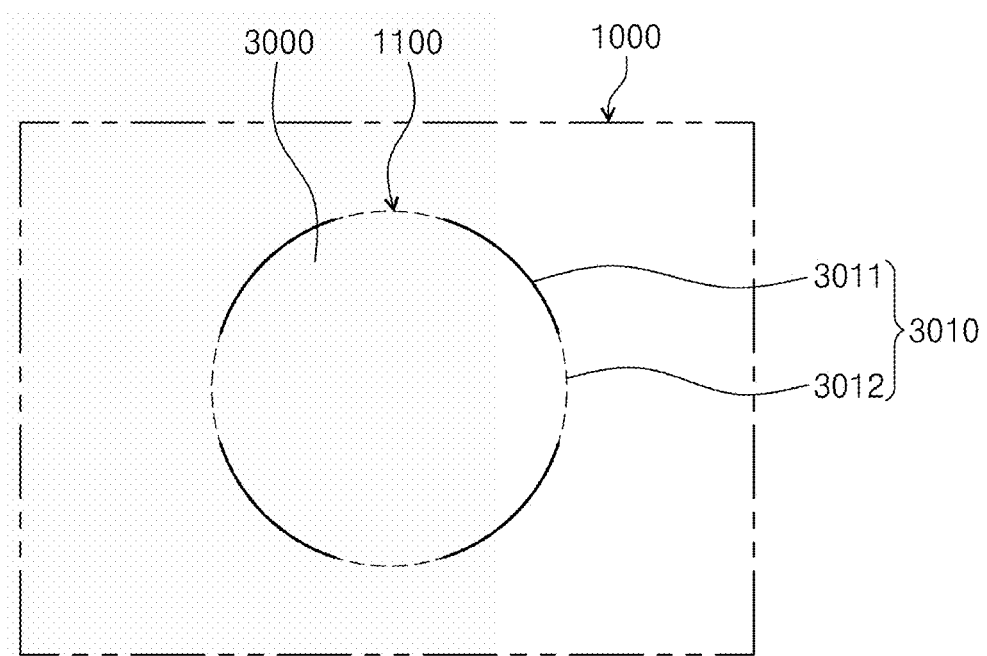
FIG. 6 is an enlarged front view of the injury opening hole illustrated in FIG. 1 with the hole cover portion connected.

FIG. 6 is an enlarged front view of the injury opening hole 1100 illustrated in FIG. 1 with a hole cover portion 3000. The hole cover portion 3000 covers the injury opening hole 1100 and is connected to the injury cover portion 1000 in the injury opening hole 1100 so that the user may easily separate it from the injury opening hole 1100 by hand. If a plurality of injury opening holes 1100 are provided, a plurality of hole cover portions 3000 may be provided to correspond to the plurality of injury opening holes 1100 respectively.

In one embodiment, the outer perimeter surface of the hole cover portion 3000 fittingly engages with, or accommodates, the inner perimeter surface of the injury opening hole 1100. That is, the hole cover portion 3000 has a shape and size that may be inserted into the injury opening hole 1100 and completely cover the injury opening hole 1100. For example, when the injury opening hole 1100 has a circular or square shape, the hole cover portion 3000 correspondingly has a circular or square shape that fittingly engages, or accommodates, the injury opening hole 1100. When the injury opening holes 1100a and 1100b have a slit shape as illustrated in FIGS. 3 and 4, the hole cover portion 3000 also has a shape corresponding to the injury opening holes 1100a and 1100b.

In one embodiment, a gap area 3010 may be positioned or located between the hole cover portion 3000 and the injury opening hole 1100 in a state where the hole cover portion 3000 is inserted into the injury opening hole 1100 and connected to the injury cover portion 1000. The gap area 3010 may include a plurality of separation areas 3011 and a plurality of connection areas 3012.

A plurality of separation areas 3011 includes areas in which the hole cover portion 3000 and the injury cover portion 1000 are separated from each other in the gap area 3010. A plurality of connection area 3012 includes areas where the hole cover portion 3000 and the injury cover portion 1000 are connected to each other in the gap area 3010. The plurality of separation areas 3011 and the plurality of the connection areas 3012 are placed or positioned alternately along the circumferential direction of the gap area 3010. The length of the connection area 3012 in the circumferential direction of the gap area 3010 is shorter than the length of the separation area 3011 in the circumferential direction of the gap area 3010. A plurality of the connection areas 3012 may be arranged to be spaced apart from each other at regular intervals. The connection area 3012 has a length in the circumferential direction of the gap area 3010 that may be easily cut by hand, but may not be easily separated due to unintentional collision or contact. Accordingly, the length of the connection areas 3012 in the circumferential direction of the gap area 3010 may vary depending on the material of the injury cover portion 1000. The length of the connection areas 3012 in the circumferential direction of the gap area 3010 may be determined through experiment.

The separation area 3011 and the connection area 3012 may be formed by a punching process while the hole cover portion 3000 is provided integrally with the injury cover portion 1000. Alternatively, the separation area 3011 and the connection area 3012 may be formed in the injury cover portion 1000 by various processing methods.

The characteristics of the gap area 3010 described above with respect to FIG. 6 may be applied to the injury opening holes 1100, 1100a, and 1100b provided in various shapes as described above.

Figure 7:
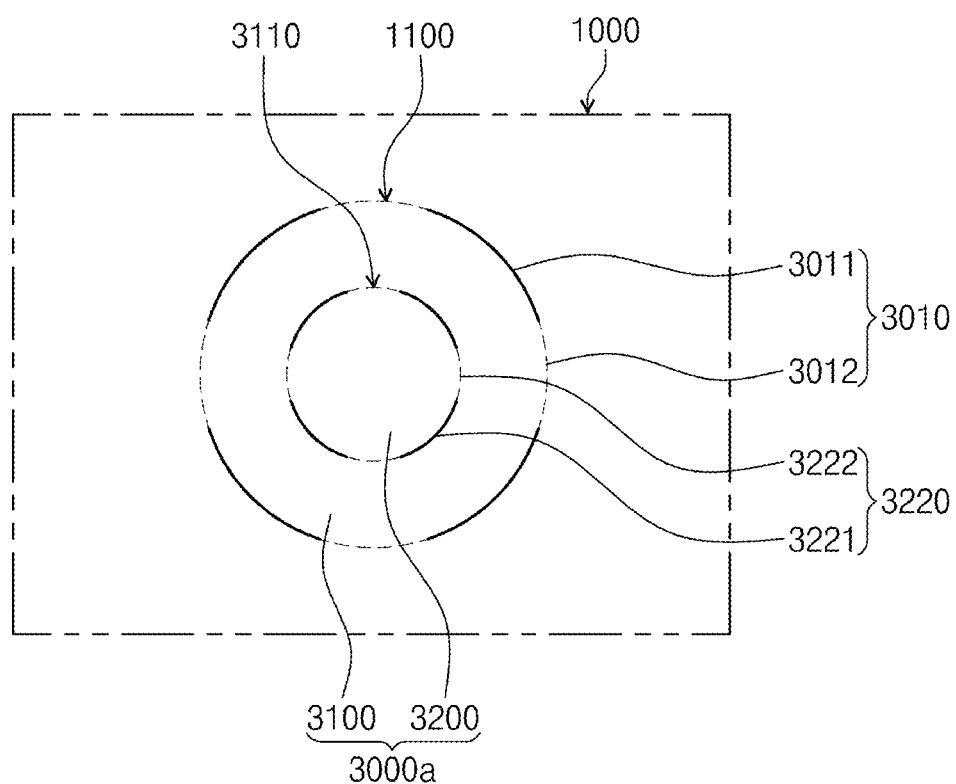
FIG. 7 is a front view illustrating a hole cover portion according to an example embodiment.

FIG. 7 is a front view illustrating a hole cover portion 3000a according to an example embodiment. The hole cover portion 3000a includes a first cover member 3100 and a second cover member 3200. The first cover member 3100 may have a structure that surrounds the second cover member 3200. For example, the first cover member 3100 and the second cover member 3200 may have a concentric circle and/or ring structure with different diameters.

The outer perimeter surface of the first cover member 3100 may engage with the inner perimeter surface of the injury opening hole 1100. A first open hole 3110 penetrating between the inner surface and the outer surface, or cutting through the thickness, of the first cover member 3100 is located in the first cover member 3100.

In one embodiment, a first gap area 3010 may be positioned between the first cover member 3100 and injury opening hole 1100 when the first cover member 3100 is inserted into the injury opening hole 1100 and connected to injury cover portion 1000. The first gap area 3010 may include a first separation area 3011 and a first connection area 3012.

The first separation area 3011 is an area in which the first cover member 3100 and the injury cover portion 1000 are separated from each other in the first gap area 3010. The first connection area 3012 is an area where the first cover member 3100 and the injury cover portion 1000 are connected to each other in the first gap area 3010. The first gap area 3010, the first separation area 3011, and the first connection area 3012 are corresponding to the first gap area 3010, the separation area 3011, and the connection area 3012 in FIG. 6 respectively. The first gap area 3010, first separation area 3011, and first connection area 3012 may have the same structure and characteristics with respect to the injury opening hole 1100 as the first gap area 3010, the separation area 3011 and connection area 3012 in FIG. 6.

The second cover member 3200 covers the first open hole 3110. The outer perimeter surface of the second cover member 3200 engages with the inner perimeter surface of the first open hole 3110.

In one embodiment, when the second cover member 3200 is inserted into the first open hole 3110 and connected to the first cover member 3100, a second gap area 3220 may be located between the second cover member 3200 and the first open hole 3110. The second gap area 3220 may include a second separation area 3221 and a second connection area 3222.

The second separation area 3221 is an area in which the first cover member 3100 and the second cover member 3200 are separated from each other in the second gap area 3220. The second connection area 3222 is an area where the first cover member 3100 and the second cover member 3200 are connected to each other in the second gap area 3220. A plurality of second separation areas 3222 and a plurality of second connection areas 3222 are provided alternately along the circumferential direction of the second gap area 3220. The length of the second connection area 3222 in the circumferential direction of the second gap area 3220 is shorter than the length of the second separation area 3221 in the circumferential direction of the second gap area 3220. A plurality of second connection areas 3222 may be arranged to be spaced apart from each other at regular intervals. The second connection area 3222 has a length in the circumferential direction of the second gap area 3220 that may be easily cut by hand, but may not be easily separated due to unintentional collision or contact. Accordingly, the length of the second connection area 3222 in the circumferential direction of the second gap area 3220 may vary depending on the material of the injury cover portion 1000. The length of the second connection area 3222 in the circumferential direction of the second gap area 3220 may be determined through experiment.

In one embodiment, the direction in which each second connection area 3222 is located from the center of the hole cover portion 3000a may coincide with the direction in which each first connection area 3012 is located from the center of the hole cover portion 3000a. Therefore, the force when tearing off the second cover member 3200 is transmitted directly to the first connection area 3012, so that compared to when the force is transmitted through the first separation area 3011, the stress concentrated in the first connection region 3012 is lowered. Accordingly, when the second cover member 3200 is torn off, the probability that the first cover member 3100 is torn off together may be reduced.

In addition, the length of the second connection area 3222 in the circumferential direction of the second gap area 3220 may be shorter than the length of the first connection area 3012 in the circumferential direction of the first gap area 3010. Therefore, the probability that the first connection area 3012 is torn apart by a force that may separate the second connection area 3222 may be reduced.

In a state in which the hole cover portion 3000a is integrated with the injury cover portion 1000, the first separation area 3011, the second separation area 3221, the first connection area 3012, and the second connection area 3222 may be formed by a punching processing method. Alternatively, the first separation area 3011, the second separation area 3221, the first connection area 3012, and the second connection area 3222 may be formed in the injury cover portion 1000 by various processing methods.

Unlike the hole cover portion 3000a of FIG. 7 having a double structure, the hole cover portion 3000 may have a triple or more multi-layer structure.

If a hole of excessive size compared to the injury 11 is opened in the injury cover portion 1000, the area supporting the body weight of the injury cover portion 1000 may become narrow, thereby lowering the weight dispersion rate. And, if a hole of a smaller size than the injury 11 is opened in the injury cover portion 1000, a problem may occur in which the injury cover portion 1000 and the injury 11 come into contact. As described above, the hole cover portion 3000a in a multiple structure allows the injury contact prevention band 100 to utilize the hole of an appropriate size for the injuries of various sizes.

The features of the first gap area 3010 and the second gap area 3220 described with reference to FIG. 7 are applicable to the injury opening holes 1100, 1100a, and 1100b provided in various shapes as described above.

Figure 8:
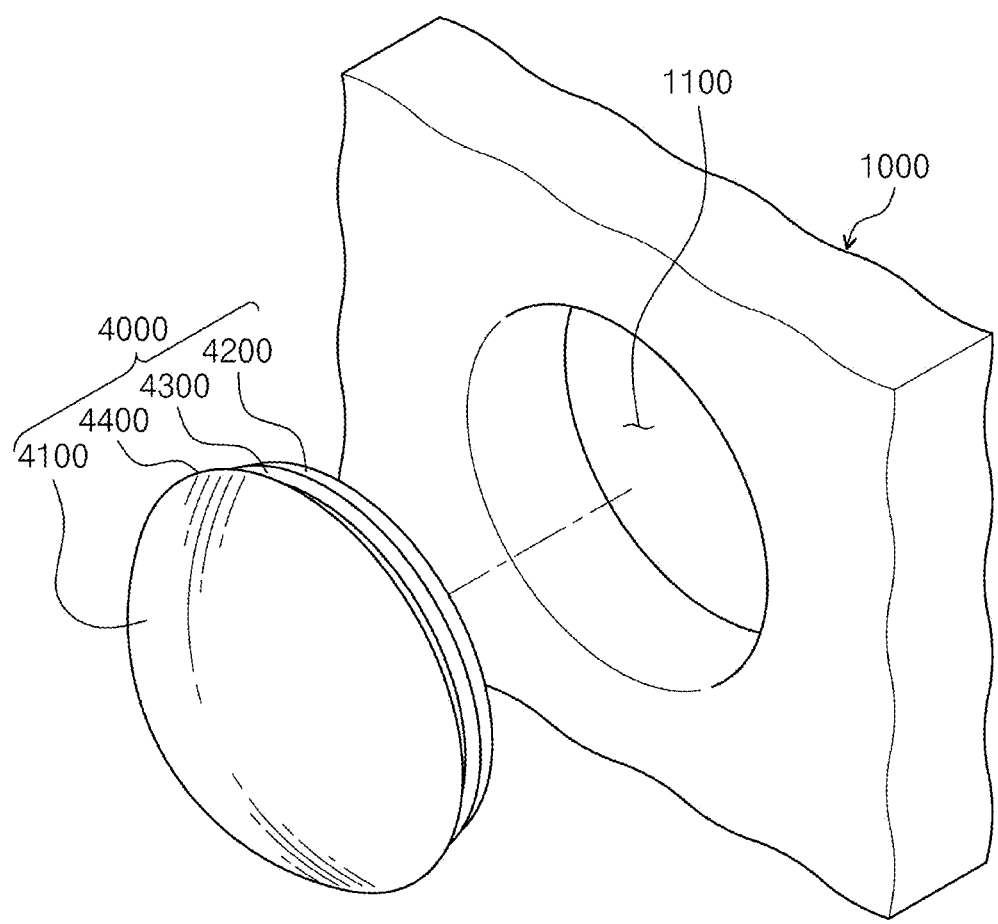
FIG. 8 is a perspective view illustrating an example of a hard cap portion.
Figure 9:
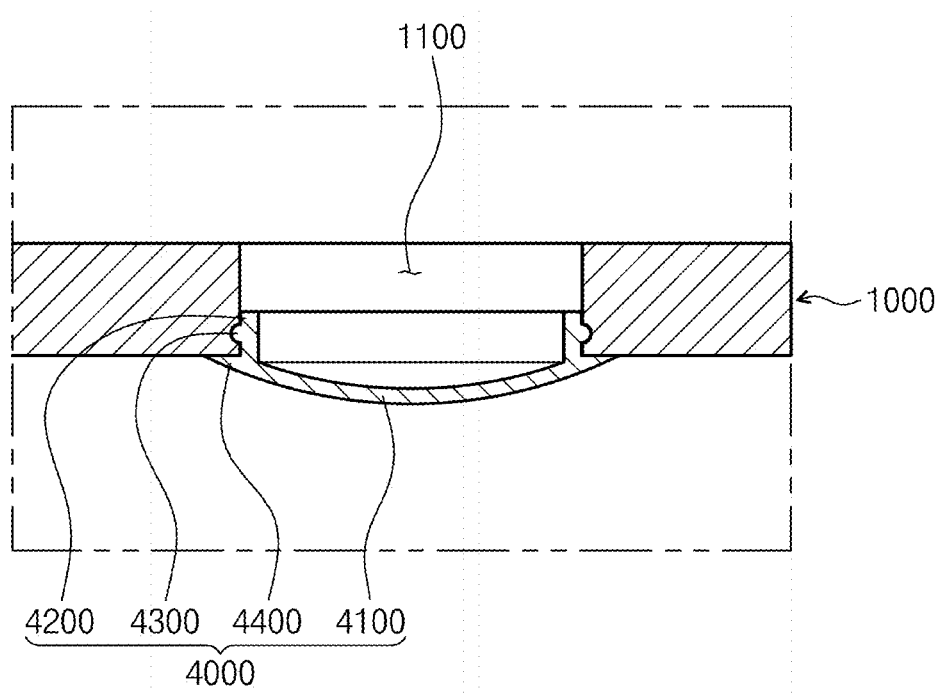
FIG. 9 is a side cross-sectional view illustrating the hard cap portion of FIG. 8 inserted into the injury opening hole.

FIG. 8 is a perspective view illustrating an example of the hard cap portion 4000. FIG. 9 is a side cross-sectional view illustrating the hard cap portion 4000 of FIG. 8 inserted into the injury opening hole 1100. Referring to FIGS. 8 and 9, the injury contact prevention band 100 may further include a hard cap portion 4000. The hard cap portion 4000 is spaced apart from the inner opening 1101 in FIG. 2 of the injury opening hole 1100 and covers the outer opening 1102 in FIG. 2 of the injury opening hole 1100. The hard cap portion 4000 is detachably fastened to the injury opening hole 1100. The hard cap portion 4000 has hardness. For example, the hard cap portion 4000 may be made of hard plastic such as phenol resin, epoxy resin, or polyester resin, or hard metal such as titanium alloy. Alternatively, the hard cap portion 4000 may be made of various hard materials. In one embodiment, the hard cap portion 4000 includes a cover wall 4100, a side wall 4200, a fastening protrusion 4300, and a fringe portion 4400.

The cover wall 4100 covers the outer opening 1102 in FIG. 2 of the injury opening hole 1100 when the hard cap portion 4000 is inserted, pushed, or pressed into the injury opening hole 1100. The cover wall 4100 has a shape and size such that outer circumference thereof engages the inner circumference of the injury opening hole 1100. For example, when the injury opening holes 1100, 1100a and 1100b are provided in a circular, square, or slit shape, the cover wall 4100 may accordingly have a circular, square, or slit shape, respectively. The cover wall 4100 may be provided in a shape that is gently convex outward. Therefore, in response to the fact that the shape of the injury cover portion 1000 is generally convex outward when wrapping around the body 10, the patient wearing it may feel a more natural comfort.

The side wall 4200 protrudes inward from the inner surface of the cover wall 4100 when the hard cap portion 4000 is inserted, pushed, or pressed into the injury opening hole 1100. The side wall 4200 may have a cylindrical shape with an outer perimeter surface fittingly engaged with the inner perimeter surface of the injury opening hole 1100.

The protrusion length of the side wall 4200 from the cover wall 4100 may be smaller than the thickness of the outer perimeter surface of the injury opening hole 1100. In one embodiment, the protrusion length of the side wall 4200 from the cover wall 4100 is shorter than a length that the cover wall 4100 may protrude from the inner opening 1101 in FIG. 2 when the injury cover portion 1000 is pressed by the body weight of the patient wearing the injury contact prevention band 100. Therefore, even when the injury cover portion 1000 is pressed by the patient wearing it, the patient may feel little or unnoticeable foreign body sensation. The protrusion length of the side wall 4200 from the cover wall 4100 may be set through simulation or experiment and/or may depend on the type of injury or wound.

The fastening protrusion 4300 protrudes from the outer perimeter surface of the side wall 4200 in the direction in which the outer perimeter surface is facing. In one embodiment, the fastening protrusion 4300 may have a single closed curve shape along the outer circumferential direction of the side wall 4200. For example, when the injury opening hole 1100 is provided in a circular shape, the fastening protrusion 4300 may have a ring shape. In another embodiment, so that the hard cap portion 4000 may be more easily inserted into the injury opening hole 1100, the fastening protrusion 4300 may be inclined so that the protrusion length from the outer perimeter of the side wall 4200 gradually becomes longer toward the outside from the end facing inward to a predetermined position. With the fastening protrusion 4300, the hard cap portion 4000 may more firmly maintain the state of being inserted into the injury opening hole 1100.

The fringe portion 4400 extends from the outer perimeter of the cover wall 4100 along the direction in which the outer perimeter surface of the side wall 4200 is facing. In one embodiment, the fringe portion 4400 has an extended length longer than the protruding length of the fastening protrusion 4300. When the hard cap portion 4000 inserted into the injury opening hole 1100, the thickness from the outer surface of the injury cover portion 1000 of the fringe portion 4400 may gradually becomes thicker toward the outside from the outer perimeter thereof to the cover wall 4100. Additionally, the outer surface of the fringe portion 4400 may have a curved shape that extends in the curved direction of the outer surface of the cover wall 4100. Therefore, when the injury cover portion 1000 is pressed by the patient, the patient may move more flexibly and the patient feels less of a foreign body sensation. Accordingly, the fringe portion 4400 may prevent the hard cap portion 4000 from being pushed into the injury opening hole 1100.

The hard cap portion 4000 may more firmly prevent contact of the injury surrounded by the inner perimeter surface of the injury opening hole 1100 and reduce penetration of external foreign substances into the injury.

When the hole cover portion 3000a has a multiple structure such as the first open hole 3110 described above, the hard cap portion 4000 may have various sizes corresponding to each hole.

Figure 10:
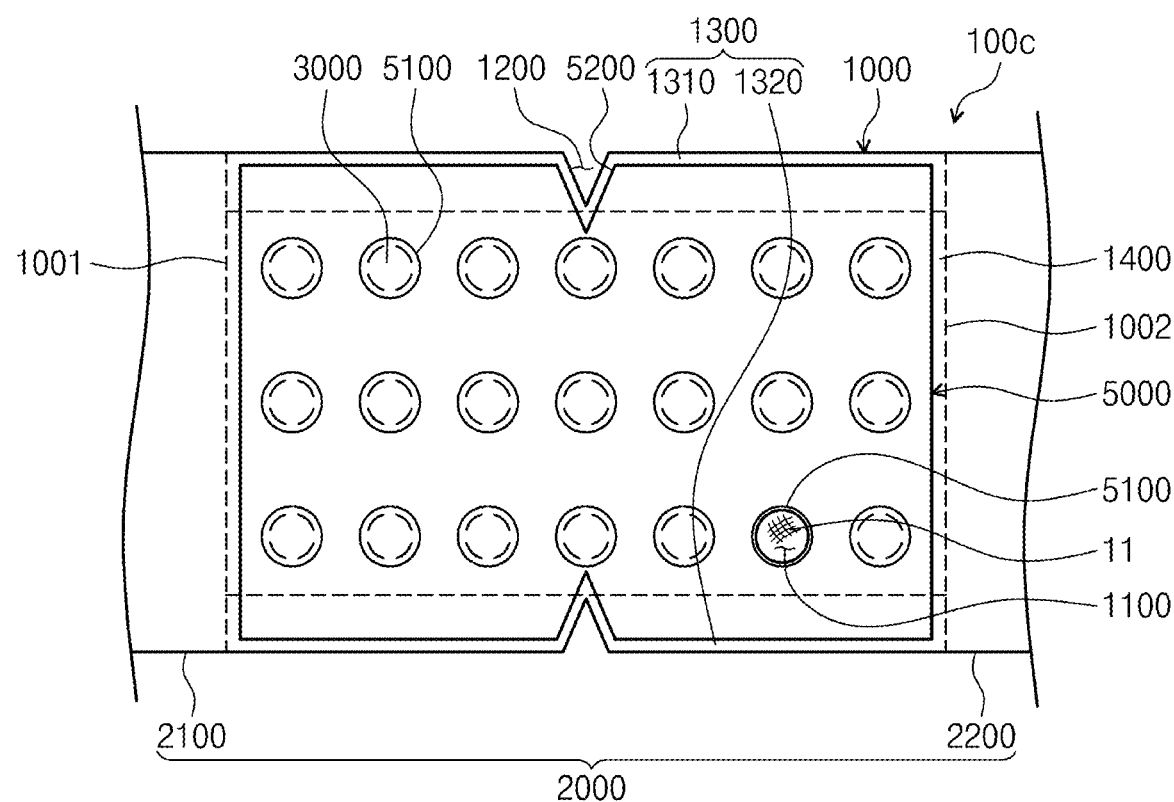
FIG. 10 is a partial front view illustrating an injury contact prevention band according to an example embodiment.

FIG. 10 is a partial front view illustrating an injury contact prevention band 100c according to an example embodiment. The injury contact prevention band 100c may further include a hard cover portion 5000.

The hard cover portion 5000 covers the outer surface of the injury cover portion 1000. The hard cover portion 5000 has hardness and ductility. The hard cover portion 5000 may be made of a metal material that has hardness and ductility. For example, the hard cover portion 5000 may be made of low carbon steel, copper, aluminum, or an alloy material containing these metal materials. the aluminum or the aluminum alloy may be the same material used for finger sprints.

An injury opening hole opening 5100 is located in the hard cover portion 5000. The injury opening hole opening 5100 cuts through the thickness of the injury cover portion 1000, or penetrates between the inner surface and outer surface of the injury cover portion 1000 to expose, reveal, show, or display the injury opening hole 1100 to the outside. In one embodiment, the injury opening hole opening 5100 has an inner circumference that surrounds the injury opening hole 1100.

The hard cover portion 5000 may be deformed according to the curvature of the body 10, so that the injury cover portion 1000 may be in close contact with the body as a whole to reduce areas of the inner surface of the injury cover portion 1000 lifted from the body 10. Therefore, the area of the injury cover portion 1000 where weight is distributed may expand, and chafing due to lifting of the injury cover portion 1000 may be prevented.

In one embodiment, a cut groove 5200 is located in the hard cover portion 5000. The cut groove 5200 is indented from the outer perimeter of the hard cover portion 5000 toward the center of the hard cover portion 5000 in a shape accommodating the cut portion 1200 at a position opposite the cut portion 1200 to expose the cut portion 1200 to the outside. When the end area 1300 is deformed according to the curvature of the body 10 the cut groove 5200 may help preventing the area opposite to the end area 1300 of the hard cover portion 5000 from bending outward or inward so that foreign body sensation may be prevented when the injury contact prevention band is worn.

When the hard cap portion 4000 is inserted, pushed, or pressed into the injury opening hole 1100, the injury opening hole opening 5100 may have an inner perimeter fittingly engaged with the outer perimeter of the fringe portion 4400, or have a size in which the inner perimeter of the injury opening hole opening 5100 is spaced apart from the fringe portion 4400 and surrounds an area adjacent to the fringe portion 4400.

The injury opening hole openings 5100 may be located at a position opposite to injury opening holes 1100 respectively, corresponding to the plurality of injury opening holes 1100.

The injury contact prevention band 100, 100a, 100b and 100c according to an example embodiment of the present disclosure may prevent contact with the injury 11 as the inner perimeter surface of the injury opening hole 1100 surrounds the injury 11. In addition, the injury contact prevention band 100 according to one embodiment of the present disclosure is lighter and has a smaller volume than bedding such as a mattress for preventing injury contact, so the injury contact prevention band 100 may be easily carried. In addition, the injury contact prevention band 100 according to an example embodiment of the present disclosure may be fastened to various parts of the body 10, and may selectively open some of the plurality of injury opening holes 1100, so that the contact with the injury at the various parts of the body 10 may be prevented. In addition, the injury opening holes 1100 corresponding to the uninjured area are not opened unnecessarily, thereby lowering the penetration rate of foreign substances, and the hole cover portion 3000 supports the body weight so that the force that the uninjured area receives may be distributed.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:
1. An injury contact prevention band comprising:
an injury cover portion to cover a part of a body including an injury; and
a fastening portion to fasten the injury cover portion to the body,
wherein the fastening portion includes:
a first flexible fastening member extending from one end of the injury cover portion,
a second flexible fastening member extending from another end of the injury cover portion, and
a connecting member detachably connecting an end of the first flexible fastening member and an end of the second flexible fastening member to each other,
wherein a plurality of injury opening holes cutting through a thickness of the injury cover portion to expose the injury, the plurality of injury opening holes being arranged along at least one direction, wherein a plurality of hole cover portions located in the plurality of injury opening holes respectively is connected to the injury cover portion so as to be separable from the plurality of injury opening holes respectively, and outer perimeter surfaces thereof fittingly engage with inner perimeter surfaces of the plurality of injury opening holes respectively, wherein gap areas are located between the hole cover portions and the injury opening holes respectively, wherein each of the gap areas includes:
  a plurality of separation areas where the plurality of hole cover portions and the injury cover portion are separated from each other, and
  a plurality of connection areas where the plurality of hole cover portions and the injury cover portion are connected to each other,
  wherein the plurality of the separation areas and the plurality of connection areas are arranged alternately along a circumferential direction of the gap areas respectively, and
  wherein the plurality of connection areas has a smaller length than the length of the plurality of separation areas, wherein the injury cover portion has a cut portion indented from an outer perimeter toward a central area in an end area between one end and the other end of an edge area thereof.

2. An injury contact prevention band comprising:

an injury cover portion configured to cover a part of a body including an injury; and a fastening portion configured to fasten the injury cover portion to the body, wherein the fastening portion includes:
  a first flexible fastening member extending from one end of the injury cover portion,
  a second flexible fastening member extending from the other end of the injury cover portion, and
  a connecting member detachably connecting an end of the first flexible fastening member and an end of the second flexible fastening member to each other, wherein a plurality of injury opening holes cutting through a thickness of the injury cover portion to expose the injury, the plurality of injury opening holes being arranged along at least one direction, and wherein a plurality of hole cover portions located in the plurality of injury opening holes respectively is connected to the injury cover portion so as to be separable from the plurality of injury opening holes respectively, and outer perimeter surfaces thereof fittingly engage with inner perimeter surfaces of the plurality of injury opening holes respectively, wherein gap areas are located between the hole cover portions and the injury opening holes respectively, wherein at least one of the gap areas includes:
  a plurality of separation areas where the plurality of hole cover portions and the injury cover portion are separated from each other, and
  a plurality of connection areas where the plurality of hole cover portions and the injury cover portion are connected to each other,
  wherein the plurality of the separation areas and the plurality of connection areas are arranged alternately along a circumferential direction of the gap areas respectively, and
  wherein the plurality of connection areas has a smaller length than the length of the plurality of separation areas, and wherein the injury cover portion has a cut portion indented from an outer perimeter toward a central area in an end area between one end and the other end of an edge area thereof.

* * * * *